(12) United States Patent
Sanger et al.

(10) Patent No.: US 10,426,366 B2
(45) Date of Patent: *Oct. 1, 2019

(54) SYSTEMS, METHODS, AND USES OF BAYES-OPTIMAL NONLINEAR FILTERING ALGORITHM

(71) Applicant: GSAcore, LLC, Los Angeles, CA (US)

(72) Inventors: Terence D. Sanger, Los Angeles, CA (US); Atiyeh Ghoreyshi, Los Angeles, CA (US)

(73) Assignee: GSACORE, LLC, Los Angeles, CA (US)

( * ) Notice: Subject to any disclaimer, the term of this patent is extended or adjusted under 35 U.S.C. 154(b) by 308 days.

This patent is subject to a terminal disclaimer.

(21) Appl. No.: 15/440,990

(22) Filed: Feb. 23, 2017

(65) Prior Publication Data
US 2017/0188867 A1    Jul. 6, 2017

Related U.S. Application Data (63) Continuation of application No. 14/762,431, filed as application No. PCT/US2014/051917 on Aug. 20, 2014, now Pat. No. 9,597,002.

(60) Provisional application No. 61/868,425, filed on Aug. 21, 2013.

(51) Int. Cl.
| | |
|---|---|
| *A61B 5/00* | (2006.01) |
| *A61B 5/04* | (2006.01) |
| *A61B 5/0492* | (2006.01) |
| *A61B 5/0488* | (2006.01) |

(52) U.S. Cl.
CPC ........ *A61B 5/04017* (2013.01); *A61B 5/0004* (2013.01); *A61B 5/0492* (2013.01); *A61B 5/4519* (2013.01); *A61B 5/486* (2013.01); *A61B 5/4836* (2013.01); *A61B 5/7203* (2013.01); *A61B 5/7264* (2013.01); *A61B 5/742* (2013.01);
(Continued)

(58) Field of Classification Search
None
See application file for complete search history.

(56) References Cited

U.S. PATENT DOCUMENTS

| | | | | |
|---|---|---|---|---|
| 5,900,835 A | * | 5/1999 | Stein | G01S 7/2922 |
| | | | | 342/159 |
| 7,974,475 B1 | * | 7/2011 | Minter | G06K 9/6278 |
| | | | | 382/159 |
| 8,311,623 B2 | | 11/2012 | Sanger | |

(Continued)

OTHER PUBLICATIONS

Terejanu et al., Adaptive Gaussian Sum Filter . . . , IEEE, vol. 56, No. 9, Sep. 2011, pp. 2151-2156 (Year: 2011).*

(Continued)

*Primary Examiner* — Kevin P Mahne (74) *Attorney, Agent, or Firm* — Cislo & Thomas, LLP (57) ABSTRACT

A stochastic Bayesian nonlinear filtering system and method that improves the filtering of noisy signals by providing efficiency, power, speed, and flexibility. The filter only requires the likelihood function p(observation|state) to determine the system state and works in various measurement models. This allows for the processing of noisy signals to be used in real time, such as in a biofeedback device that senses noisy surface electromyography muscle electrical activity, filters the sensed signal using the nonlinear filtering method, and provides vibrations based on the muscular activity.

2 Claims, 8 Drawing Sheets

(52) U.S. Cl.
CPC .......... *A61B 5/7455* (2013.01); *A61B 5/0488* (2013.01); *A61B 2560/0475* (2013.01)

(56) References Cited

U.S. PATENT DOCUMENTS

| | | | | |
|---|---|---|---|---|
| 8,577,539 | B1* | 11/2013 | Morrison | G01C 21/165 |
| | | | | 701/28 |
| 8,725,456 | B1* | 5/2014 | Saha | G05B 23/0283 |
| | | | | 702/181 |
| 9,139,203 | B2* | 9/2015 | Moshchuk | B60W 30/12 |
| 2003/0233197 | A1 | 12/2003 | Padilla et al. | |
| 2005/0038638 | A1 | 2/2005 | Comaniciu | |
| 2007/0112566 | A1* | 5/2007 | Chen | G10L 15/14 |
| | | | | 704/240 |
| 2007/0147661 | A1* | 6/2007 | Fukaya | G06K 9/00248 |
| | | | | 382/104 |
| 2008/0021342 | A1 | 1/2008 | Echauz et al. | |
| 2008/0056535 | A1* | 3/2008 | Bergmann | G01C 21/30 |
| | | | | 382/103 |
| 2009/0074038 | A1* | 3/2009 | Lentmaier | G01S 19/22 |
| | | | | 375/148 |
| 2009/0209878 | A1 | 8/2009 | Sanger | |
| 2010/0274102 | A1* | 10/2010 | Teixeira | A61B 5/14552 |
| | | | | 600/301 |
| 2011/0231016 | A1* | 9/2011 | Goulding | G06N 3/008 |
| | | | | 700/246 |
| 2011/0291887 | A1* | 12/2011 | Pulford | G01S 19/20 |
| | | | | 342/357.58 |
| 2011/0301436 | A1 | 12/2011 | Teixeira | |
| 2012/0277545 | A1 | 11/2012 | Teixeira | |
| 2015/0051880 | A1* | 2/2015 | Arditti Ilitzky | G06F 17/5009 |
| | | | | 703/2 |
| 2015/0340027 | A1* | 11/2015 | Wang | G10L 15/07 |
| | | | | 704/221 |

OTHER PUBLICATIONS

Maciejowski et al., Nonlinear Filter Design Using FPK Probability Density, IEEE vol. 36, Issue 1, Jan. 2000, pp. 309-315. (Year: 2000).*

Arasartnam et al. Discrete-Time Nonlinear Filtering Algorithms . . . , IEEE vol. 95, Issue 5, May 2007, pp. 953-977. (Year: 2007).*

Panta et al., Data Assoc. and Track Mang. For the Gaussian Mixture Probability . . . , IEEE vol. 45, Issue 3, Jul. 2009, pp. 1003-1016 (Year: 2009).*

Daum, Nonlinear Filters: Beyond the Kalman Filter, IEEE vol. 20, No. 8, Aug. 2005, pp. 57-69, (Year: 2005).*

Brockwell et al., Recursive Bayesian Decoding of Motor Cortical Signals by Particle Filtering, Scientific Paper, 2003.

Pavlovic, Dynamic Bayesian Networks for Information Fusion with Applications to Human Computer Interfaces, Scientific Paper, 1999.

* cited by examiner

SYSTEMS, METHODS, AND USES OF BAYES-OPTIMAL NONLINEAR FILTERING ALGORITHM

CROSS-REFERENCE TO RELATED APPLICATION

This patent application is a continuation of U.S. patent application Ser. No. 14/762,431 entitled "Systems, Methods and Uses of Bayes-Optimal Nonlinear Filtering Algorithm," filed Jul. 21, 2015, which is a Section 371 national stage application of PCT application PCT/US2014/051917, filed Aug. 20, 2014, which claims the benefit of U.S. Provisional Patent Application Ser. No. 61/868,425, entitled "Bayes-Optimal Nonlinear Filtering Algorithm," filed Aug. 21, 2013, which applications are incorporated in their entirety here by this reference.

TECHNICAL FIELD

This invention relates to signal processing using filters and more particularly to a new stochastic Bayesian filtering method to filter continuous non-linear noisy signals.

BACKGROUND

When there is poor-quality or distorted sensor data that is being used to measure a time-varying process, a nonlinear filter/estimator extracts underlying important time-varying information. For example, a camera pointed at a road in front of a car driving on a foggy night may generate poor-quality data of the road location relative to the car, and the road location may be time-varying due to steering movements and curves in the road. A nonlinear filter may be useful for estimating the road location relative to the car in order to assist the driver to make corrective movements. In another example, radar is used to track the position of a moving object. A nonlinear filtering algorithm would be useful for estimating the location of the moving object from poor-quality and distorted radar.

Common types of noise include sensor noise from cameras and other imaging systems, radar, ultrasonic range sensors, X-rays, microphones, and ambient sources of noise. Common types of distortion include quantization (encoding continuous measurements using a small number of bits in a computer). The Bayes-optimal nonlinear filtering algorithm is at least as good as current algorithms at handling noise, and is much better at handling quantization and other computational distortions.

Current State of the Art

Filtering techniques are employed to estimate the hidden state of a dynamical system from noisy measurements. They do so using a model of the underlying dynamics and a measurement model that links observed variables to the hidden states. When sensor measurements used for feedback control are noisy, quantized, intermittent, ambiguous, or otherwise bandlimited, then filtering algorithms must be used by the observer process to extract the best possible estimate of the current state. The commonly used algorithms are based on linear system and observation models and samples taken either in discrete time (e.g., Kalman filter) or continuous time (e.g., Kalman-Bucy filter). The Extended Kalman Filter (EKF), Unscented Kalman Filter (UKF) and their variations are approximate solutions that can be applied to nonlinear systems, but these filters are not optimal and they may have poor performance when the noise distribution is non-Gaussian. Although, unlike EKF, UKF does not require differentiability of the dynamics and measurement models, it estimates only the first and second order statistics of the state density. These are only sufficient statistics for processes that remain Gaussian distributed at all times (which is almost never the case when the dynamics are nonlinear). Thus for all Kalman filter variants there is a strong assumption that the probability distribution of the state remains unimodal (usually Gaussian). More complex distributions (such as those with hard boundaries, multiple possible values, or discrete values) cannot be represented. Recent extensions such as the use of Gaussian mixture models for the density estimate permit more flexibility but still have significant limitations on the form of the density and the measurement models.

Improvements in processing speed have permitted a class of filtering algorithms to be developed that apply to nonlinear dynamic systems, nonparametric uncertainty models, and nonlinear observation models. This class is commonly referred to as "nonlinear filters", although it may be more accurate to describe it as "nonparametric filters" or "Bayesian filters" because the distinguishing feature is estimation of the nonparametric representation of the full density p(x,t) at each time t, rather than just the first and second-order statistics.

Particle filters are perhaps the most well-known implementation of nonlinear filters, but they only apply when observations are taken at discrete time intervals. For continuously observed processes, the only currently known nonlinear (nonparametric) filters are the Kushner and Zakai filters that assume that observations are given by $$dz = h(x)dt + dB$$

where B is Brownian noise, and h(x) is a deterministic and possibly nonlinear, nondifferentiable, or noninvertible function. This makes the technical assumption that the state is related to the derivative of the observation process; common observation models such as z=x cannot be represented.

Currently existing nonlinear filters are limited due to the requirements and assumptions assumed by the filters. Consider a process with the following stochastic differential equation for the state:

$$dx = f(x)dt + g(x)dW$$

where W is Brownian noise, x is state, and f(x) and g(x) are nonlinear differentiable functions that model the deterministic dynamics of state and the state-dependent noise, respectively. For this class of smoothly-evolving Markovian system dynamics, the probability density of state evolves approximately according to the linear partial differential Fokker-Planck equation:

$$\frac{\partial p}{\partial t} = -\frac{\partial (fp)}{dx} + \frac{1}{2}\frac{\partial^2 (g^2 p)}{dx^2}$$

where p=p(x,t) is the pdf of state. This can be written as $\dot{p}=Fp$, where F is the linear Fokker-Planck operator on p, and $\dot{p}$ indicates the partial differential with respect to t.

The Extended Kalman Filter (EKF) with observation model z=h(x) requires calculation of the Jacobians df/dx and dh/dx, and it therefore assumes that f and h are both differentiable. Both the EKF and the UKF assumed that p(x,t) can be approximated by a Gaussian, so that first and second-order statistics are sufficient. But note that for almost all nonlinear functions f(x), even when p(x,t0) is Gaussian, p(x,t) is unlikely to be Gaussian when t>t0. Common examples include non-uniform distributions of flow, container or obstacle boundaries, or repulsive forces.

The Zakai filter is given by the stochastic partial differential equation:

$$dp = Fp\,dt + h^T R^{-1} dz\, p$$

and the Kushner filter is:

$$dp = Fp\,dt + (h - \bar{h}_t)^T R^{-1} (dz - \bar{h}_t dt) p$$

where $\bar{h}_t$ is the expected value over x of h(x) at time t, dz is the differential of the observation process, R is the autocorrelation of the observation noise, and h is to be interpreted as the function h(•). Unlike EKF, h does not have to be differentiable. However, note that the observation process z is the integral of h(x) and thus often unbounded.

Although the Zakai equation is mathematically equivalent to the Kushner equation up to normalization, in practice it seems to diverge from solutions of the Kushner equation due to numerical sensitivity.

These existing filters for continuous-time measurement, including variants on the Kalman filter, Gaussian-mixture models, and the Kushner and Zakai filters, require observations whose means are determined by algebraic functions of the state, and all other statistics are independent of state. Thus there are no filters that apply when observations are a Poisson process with rate x, a Gaussian process with variance x, or other stochastic models in which the uncertainty of the observation depends on the state.

For example, in the human nervous system, it is very common for the firing rate of neurons to be regulated by an underlying continuous variable like muscle length or force as is the case for the muscle spindle or Golgi tendon organs. In these cases, the underlying state variable is measured through a Poisson process, where the rate of the process is a function of the state. As such, there is no explicit algebraic equation describing the observation process. Therefore, this observation model cannot be handled by either Kalman Kushner, or Zakai equations, or their extensions for use in filtering the signal.

Therefore there is a need for a new class of continuous-time nonlinear filter with a much more general observation model that requires only specification of the conditional density of the observation given the state p(z|x). This new filter should achieve the upper bound on information extraction from the data, so that the rate of change of entropy of the state density estimate is equal to the mutual information between the observation and the state.

SUMMARY OF INVENTION

In light of the foregoing, it is apparent that there exists a need for a nonlinear filter that may be applied to noisy signals with different observation models, including Gaussian, Gamma, and Poisson models. Hence, it is an object of the present invention to design a filtering method with great flexibility in the observation model.

This is provided by the new Bayes-optimal nonlinear filtering method. This method uses a new algorithm that is very efficient and powerful compared to the state of the art because the only knowledge about the observed variable that is needed is the likelihood function p(observation|state). This method integrates to Bayes' Rule in the limit, which suggests its optimality.

The algorithm of the Bayes-optimal nonlinear filtering method is described by a partial differential equation. The purpose of the algorithm is to filter a nonlinear signal by combining noisy measurements of the signal with an internal estimate of the current probability distribution for the signal. The differential equation provides a model and algorithm that applies to continuous signals with continuous or intermittent measurements. It improves upon current methods because it can be shown to integrate to Bayes rule and therefore to be optimal in the sense of Bayesian estimation (maximum probability of finding the correct answer at every time point). There are potential applications in aerospace, automotive, audio, telephony, chemical reaction, robotic, and consumer filtering, estimation, and control algorithms.

This Bayes-optimal nonlinear filter is very useful for filtering noisy signals. Some areas that notably have noisy signals include:

Filtering of noisy cellular radio signals, or filtering noise in the resulting audio signal, for use in low-power and ultra-low-power cellular telephony, or when cellular telephones must be used under conditions of poor radio reception or high interference.

Filtering and decoding of wide-band, spread-spectrum, or pseudo-random radio, telephone, or other communications signals, thus permitting wide-band spread-spectrum or pseudo-random encoding and transmission of signals.

Target tracking, including: marker-less motion capture; surgical procedures; and Multiple object tracking (e.g., tracking cars from a satellite image).

Measurement for control systems, including: aircraft sensor processing for stabilizing controllers and autopilots; cruise control and lane control algorithms (self-driving or error-detecting cars); and chemical process control from noisy sensor measurements.

Sound processing, including filtering existing recordings or cleaning up live microphone recordings (similar to the Dolby Labs business model).

Sound processing for telephony.

Image Processing, including removing noise from images.

Video Processing, including removing noise from video.

Analog to digital converter filtering and improved resolution.

Sensory fusion, multi-sensory data (Robotics).

Highly distributed sensing (multiple sensors or cameras looking at the same thing, and using all that data for estimation)

Brain-machine interface: interpreting firing of multiple neurons in the brain in order to let paralyzed people control a computer Medical applications: identifying the location of targets for stereotactic surgery.

In some embodiments, noisy signals may comprise noisy image data or other types of sensor data, and the goal is to estimate the location of one or more objects. For example, in a target tracking scenario, the one or more objects could include military targets, humans from surveillance video, identifying body parts in images to use for video games (e.g., Kinect controller) or computer input, automatic camera positioning for sports (e.g., following a particular player) or spotlight positioning for performances, etc.

In other embodiments, the Bayes-optimal nonlinear filtering method is utilized in medical devices, such as to filter surface EMG data that is inherently noisy due to the way data is captured. In such an embodiment, the filtered data could be utilized in real time to produce feedback and analysis of a subject's muscle behavior, encouraging increased muscle usage for rehabilitation.

Utilizing the Bayes-optimal nonlinear filter will also increase accuracy and precision in signal processing. This also removes the latency introduced by excess low-pass filtering. The increased quality of the filter gives more flexibility in choosing the quality of sensors. This allows a reduction in the cost of hardware components, as sensing devices would not be required to be as precise to achieve the same quality of data. The Bayes-optimal nonlinear filtering method implementations may include, but are not limited to, software stored on non-transitory storage media, associated computing hardware designed to run the software, and dedicated hardware such as a dedicated nonlinear filter chip with the algorithms embedded in VLSI.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The new Bayes-optimal nonlinear filtering method initializes a probability distribution function based on the observation model and continually updates the pdf for each observation while providing a maximum likelihood estimate of the state. The Bayes-optimal nonlinear filter equation used for unknown state x(t) and observations z(t) with a known memoryless observation model p(z(t)|x(t)) is given by $$\frac{\partial p(x, t)}{\partial t} = Fp(x, t) + [\log p(z \mid x) - \log p(z, t)] p(x, t)$$

where z is the current observation, p(z|x) is the observation model, $p(z,t) = \int p(z|x)p(x,t)dx$ is the scalar probability of observing z given the current pdf estimate, and F is the Fokker-Planck operator given by $$Fp = -\frac{\partial (fp)}{dx} + \frac{1}{2}\frac{\partial^2 (g^2 p)}{dx^2}$$

We can show that this new filtering equation is the continuous-time limit of the discrete Bayesian update equation:

$$p(x, t + \Delta t) = \frac{p(z(t + \Delta t) \mid x)}{p(z(t + \Delta t))} Mp(x, t) = B_z Mp(x, t)$$

where M is the Markov update operator that is the short-time solution to the Fokker-Planck equation over Interval $\Delta t$, and $B_z$ is a diagonal operator that implements the Bayesian update of x at time $t+\Delta t$. B is defined so that for any prior density p(x), $$B_z p(x) = \frac{p(z \mid x) p(x)}{p(z)}.$$

Thus Mp(x,t) is the estimate of $p(x, t+\Delta t)$ immediately prior to making a (discrete) observation $z(t+\Delta t)$, and BzMp(x,t) is the posterior estimate of $p(x,t+\Delta t)$ immediately after observing $z(t+\Delta t)$.

To illustrate this, note that iteration of the previous update equation gives $p(x,T) = (\Pi B_{z(ti)} M) p(x, 0)$ and the math is simplified if we assume a countable basis for the space of realizable probability densities, and if z(t) is constant over the short interval, then we can write this as:

$$p(x, T) = e^{\sum (\log B_{z(t_i)} + \log M)} p(x, 0)$$

where log B is defined by the log of its (diagonal) elements, and log M is defined such that exp(log M)p=Mp for all realizable p. Since M is the solution of the Fokker-Planck equation $\dot{p}=Fp$ which for short intervals has quasi-static solution $\exp(F \Delta t)$, we see that we can identify log M with F. Letting $\Delta t \to 0$, we write:

$$p(x,T) = e^{\int (\log B_{z(t)} + F) dt} p(x,0)$$

which is the solution of the differential equation $$\dot{p}(x,t) = (\log B_{z(t)} + F) p(x,t)$$

This is equivalent to the Bayes-optimal nonlinear filter equation.

Figure 1A:
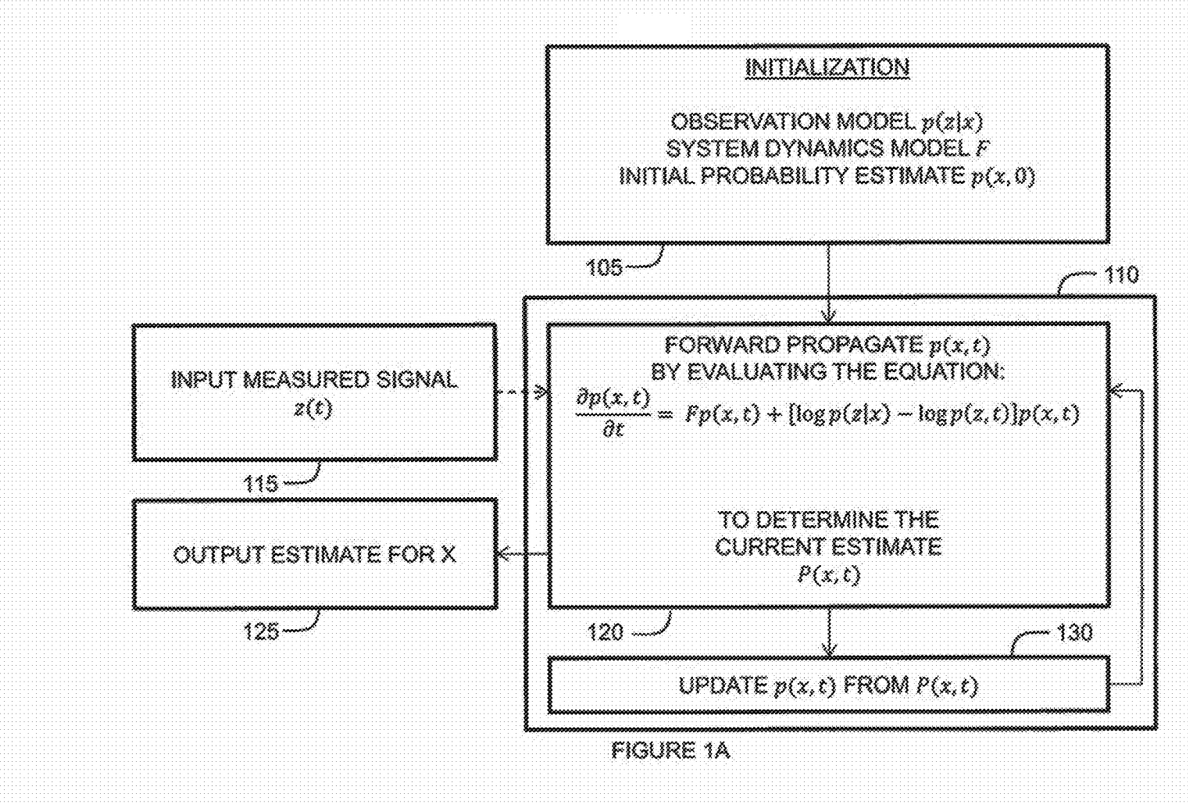
FIG. 1A shows a flow diagram of a nonlinear filtering algorithm in accordance with an embodiment of the present disclosure.

The method steps of FIG. 1A show a framework from which to apply the new filtering equations to a noisy signal. This framework supports various observation/measurement models and allows for input of the specific models to more accurately estimate the maximum likelihood estimate of the state MLest(x(t)).

The filter is first initialized in step 105. At this step, the observation model, system dynamics model, and initial probability estimate are determined. The Initialization determinations vary depending on the problem specification, as shown in the embodiment illustrated in FIG. 1B.

The observation model determines the conditional probability density p(z|x). This describes memoryless observations that can be deterministic, nondeterministic, nonlinear, or noninvertible. The observation model takes into account if the signal has been pre-filtered, rectified, or processed in any way. It also takes into account the sources of error, noise distribution, number of parameters, rate of events, and the like. Examples of sources of error and inaccuracy include, but are not limited to, signal dependent noise, malicious introduction of errors, fixed or variable delay, invertible nonlinearities (including lossless data compression and compressed sensing), noninvertible nonlinearities (including quantization and lossy data compressions), crosstalk, bit errors, and any other form of invertible or noninvertible deterministic or stochastic mapping between the desired signal and the measurement. Examples of observation models include, but are not limited to, Gaussian, Gamma, Poisson, and Laplace models.

The system dynamics model F represents what happens in the absence of observations. The dynamics model allows for the Bayes-optimal nonlinear filter to continuously output a best estimate of the state even in the absence of an observation. A typical system dynamics model would be given by the Fokker-Planck equation. However, F may take another form depending on the problem specification.

The initial probability estimate p(x,0) represents the prior information available before making any observations, and it is often taken as uniform (for bounded domains), Gaussian (for unbounded domains), or a delta-function (when initial conditions are precisely known).

The input measured signal z(t) in step 115 is used in the forward propagation step 120. The input measured signal z(t) may be amplified, pre-filtered, rectified, or manipulated in various ways, which are taken into account when determining p(z|x).

The recursive algorithm 110 continuously forward propagates the probability distribution function p(x,t) in step 120, outputs the maximum likelihood estimate of the state in step 125, and normalizes the probability distribution function (if necessary) for the next propagation in step 130. In the first forward propagation, the initial probability estimate p(x,0) from step 105 is used, while in subsequent forward propagations, the normalized probability estimate p(x,t) from step 130 is used. The forward propagation of p(x,t) in step 120 also uses the observation model p(z|x), system dynamics model F, and measured signal z(t) if available. These variables are used to forward propagate the probability density function p(x,t) by evaluating the equation given by:

$$\frac{\partial p(x,t)}{\partial t} = Fp(x,t) + [\log p(z|x) - \log p(z,t)] p(x,t)$$

Evaluating the equation includes evaluating equations derived from and/or equations equivalent to the above equation. By integrating the Bayes-optimal nonlinear filtering equation, the current probability estimate (posterior probability density function) P(x,t) is determined. The output is then determined by finding an estimate of the hidden state x in step 125. The estimate may be determined, by way of example and not limitation, by analyzing P(x,t) to find the maximum-likelihood, maximum a posteriori, mean, median, mode, and other types of estimates.

The probability distribution function p(x,t) is updated from P(x,t) in step 130 for upcoming calculations in the recursive algorithm. In some embodiments, the probability distribution function p(x,t) is updated with the values of the posterior probability density function P(x,t). In some embodiments, p(x,t) is updated by normalizing P(x,t). Normalization may be determined by whether the recursive algorithm is using a normalized version or non-normalized version of the algorithm. In some embodiments, the probability distribution function p(x,t) is only normalized as needed to account for drift and/or other factors. After normalization, the probability estimate p(x,t) should satisfy the following conditions: $0 \leq p(x,t) \leq 1$ for all values, and $\int p(x,t) dx = 1$.

The Bayes-optimal filtering algorithm allows continuous time measurements. Rather than requiring a measured signal at every update, the algorithm takes into account the absence of measured data and adds the components of the forward propagation and the measurement effect at every timestep. At every timestep, the state updates in step 120 continuously and data z(t) is incorporated from step 115 whenever it becomes available. This algorithm is simpler than previous continuous algorithms, and the sampling rate can be arbitrarily fast.

The measurement models in step 105 may be estimated or simplified based on various factors. Since p(z,t) is a scalar, its effect is to normalize the probability density, and if this term is eliminated the effect is to produce a non-normalized estimate of the density:

$$\frac{\partial p(x,t)}{\partial t} = Fp + [\log p(z|x)] p(x,t)$$

For exponential-family observation models with unknown dynamics, this leads to a particularly simple form of the estimation equation. For example, in a specified problem having unit variance additive Gaussian noise, $\log p(z|x) = -(z-x)^2$, this leads to:

$$\frac{\partial p(x,t)}{\partial t} = Fp - \frac{1}{2}(z-x)^2 p(x,t)$$

Unit width Laplace-distributed noise leads to:

$$\frac{\partial p(x, t)}{\partial t} = Fp - |z - x|p(x, t)$$

Additional equations may be derived from the Bayes-optimal nonlinear filtering algorithm dependent on the specified conditions as shown in these examples, and are parts of embodiments of the present disclosure used in the Bayes-optimal framework.

Figure 1B:
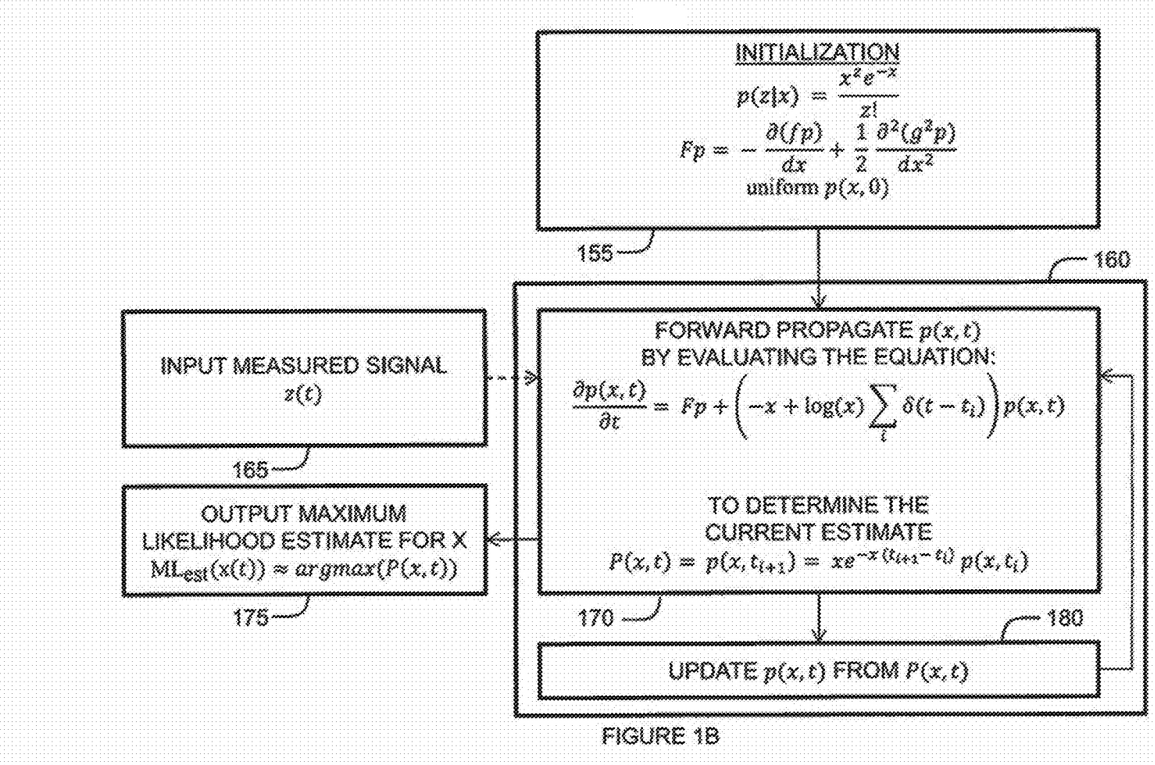
FIG. 1B shows a flow diagram of a nonlinear filtering algorithm using a Poisson measurement model in accordance with an embodiment of the present disclosure.

FIG. 1B shows how choosing a measurement model and estimation equation fits into the Bayes-optimal nonlinear filtering method framework. In step 155, a Poisson measurement model, a system dynamics model determined by the Fokker-Planck equation, and uniform initial probability estimate are initialized. This observation model is a non-homogenous Poisson process with rate x(t), the observations are a series of event times $t_i$, and the non-normalized estimation equation in step 170 is given by $$\frac{\partial p(x, t)}{\partial t} = Fp + \left(-x + \log(x)\sum_i \delta(t - t_i)\right)p(x, t)$$

where $\delta(t-t_i)$ is a Dirac delta-function centered at the time of an event. This can be implemented by having the state evolve according to $\dot{p}=Fp-xp$ between events, and assigning $p \leftarrow xp$ at the time of each event. Integration of this equation between $t_i$ and $t_{i+1}$ for constant x (and leaving out the term Fp for simplicity) yields $$p(x, t_{i+1}) = xe^{-x(t_{i+1}-t_i)}p(x, t_i)$$

which is the standard equation for the probability of rate x given an inter-event interval of $t_{i+1}-t_i$.

In various embodiments, the method steps described herein, including the method steps described in FIGS. 1A and 1B, may be performed in an order different from the particular order described or shown. In other embodiments, other steps may be provided, or steps may be eliminated, from the described methods.

Systems, apparatus, and methods described herein may be implemented using digital circuitry, or using hardware using well known processors, memory units, storage devices, computer software, and other components. Typically, hardware includes a processor for executing instructions and one or more memories for storing instructions and data. A computer may also include, or be coupled to, one or more storage devices, such as one or more magnetic disks, internal hard disks and removable disks, optical disks, etc.

Figure 2:
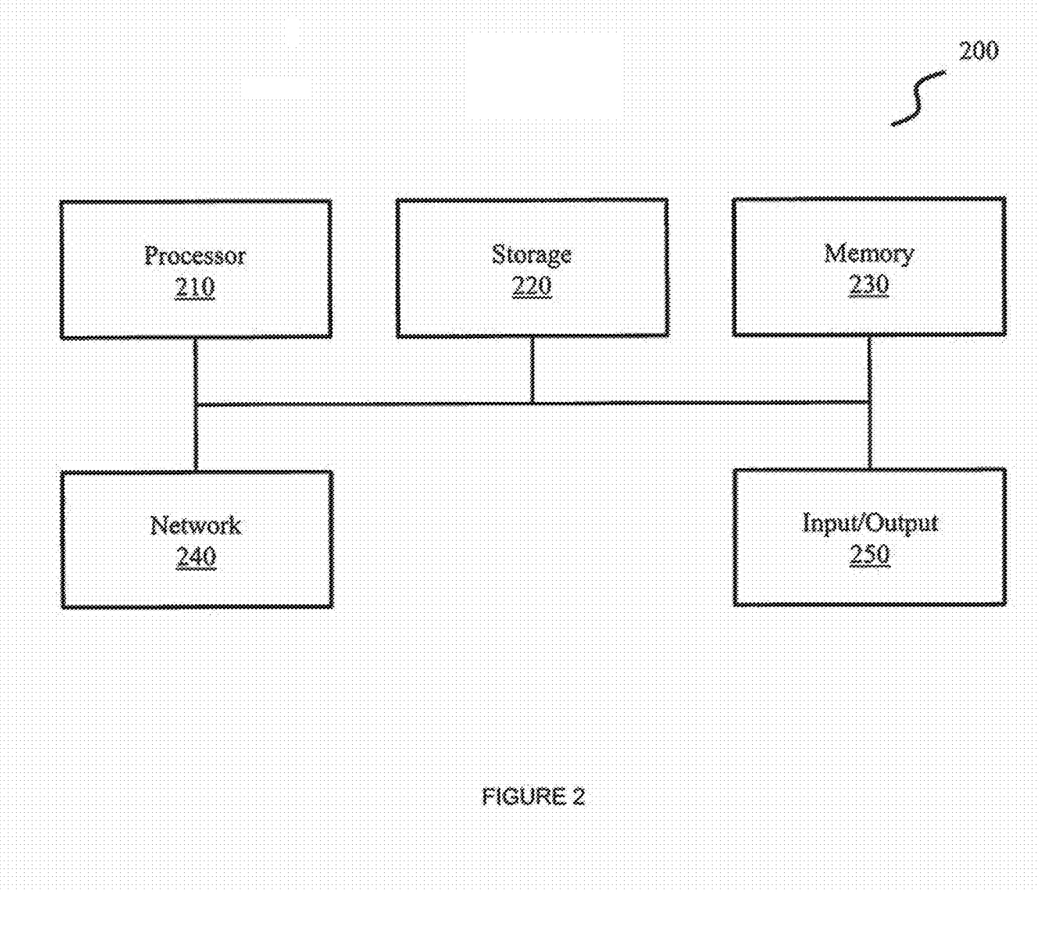
FIG. 2 shows a high level diagram of hardware that may be used to implement various aspects of the present disclosure in certain embodiments.

A high-level block diagram of hardware 200 that may be used to implement systems, apparatus, and methods described herein is illustrated in FIG. 2. The hardware 200 comprises a processor 210 operatively coupled to a data storage device 220 and memory 230. Processor 210 controls the overall operations of the hardware 200 by executing program instructions that define such operations. The program instructions may be stored in data storage device 220, or other non-transitory computer readable medium, and loaded into memory 230 when execution of the program instructions is desired. Thus, the method steps of FIG. 1 can be defined by the program instructions stored in memory 230 and/or data storage device 220 and controlled by processor 210 executing the computer program instructions. For example, the program instructions can be implemented as executable code programmed by one skilled in the art to perform an algorithm defined by the method steps in FIG. 1. Hardware 200 also includes an input/output interface 250 in order to receive input, such as a noisy signal z, and output filtered results, such as a maximum likelihood estimate of x. Hardware 200 may also include a network interface 240 in order to communicate with other devices via a network.

Processor 210 can include, among others, special purpose processors with software instructions incorporated in the processor design and general purpose processors with instructions in storage device 220 or memory 230, to control the processor 210, and may be the sole processor or one of multiple processors of hardware 200. Processor 210 may be a self-contained computing system, containing multiple cores or processors, a bus, memory controller, cache, etc. A multi-core processor may be symmetric or asymmetric. Processor 210, data storage device 220, and/or memory 230 may include, be supplemented by, or incorporated in, one or more application-specific integrated circuits (ASICs) and/or one or more field programmable gate arrays (FPGAs). It can be appreciated that the disclosure may operate on a computer with one or more processors 210 or on a group or cluster of computers networked together to provide greater processing capability.

Data storage device 220 and memory 230 each comprise a tangible non-transitory computer-readable storage medium. By way of example, and not limitation, such non-transitory computer-readable storage medium can include random access memory (RAM), high-speed random access memory (DRAM), static random access memory (SRAM), double data rate synchronous dynamic random access memory (DDRAM), read-only memory (ROM), erasable programmable read-only memory (EPROM), electrically erasable programmable read-only memory (EEPROM), flash memory, compact disc read-only memory (CD-ROM), digital versatile disc read-only memory (DVD-ROM) disks, or other optical disk storage, magnetic disk storage or other magnetic storage devices, or any other medium which can be used to carry or store desired program code means in the form of computer-executable Instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Network/communication interface 240 enables the computer 200 to communicate with networks, such as the Internet, an intranet and/or a wireless network, such as a cellular telephone network, a wireless local area network (LAN) and/or a metropolitan area network (MAN), and other devices using any suitable communications standards, protocols, and technologies. By way of example, and not limitation, such suitable communications standards, protocols, and technologies can include Ethernet, Wi-Fi (e.g., IEEE 802.11), Wi-MAX (e.g., 802.16) Bluetooth, near field communications (NFC, radio frequency systems, infrared, GSM, EDGE, HS-DPA, CDMA, TDMA, quadband, VoIP, IMAP, POP, XMPP, SIMPLE, IMPS, SMS, or any other suitable communications protocols. By way of example, and not limitation, the network interface 240 enables the hardware 200 to transfer data, synchronize information, update software, or any other suitable operation.

Input/Output interface 250 allows the hardware 210 to receive and send information to and from devices/hardware.

For example, the nonlinear filter receives a signal as an input, and outputs the maximum likelihood of the state of the signal. An example input device can include a measurement device to send measurements to be filtered by the hardware 210, such as an electrode for sensing surface electromyography muscle electrical activity. An example output device can include a feedback device that receives the filtered signal and produces vibrations dependent on the strength of the filtered signal.

Any or all of the systems and apparatus discussed herein, may be implemented using hardware such as shown in FIG. 2.

Figure 3:
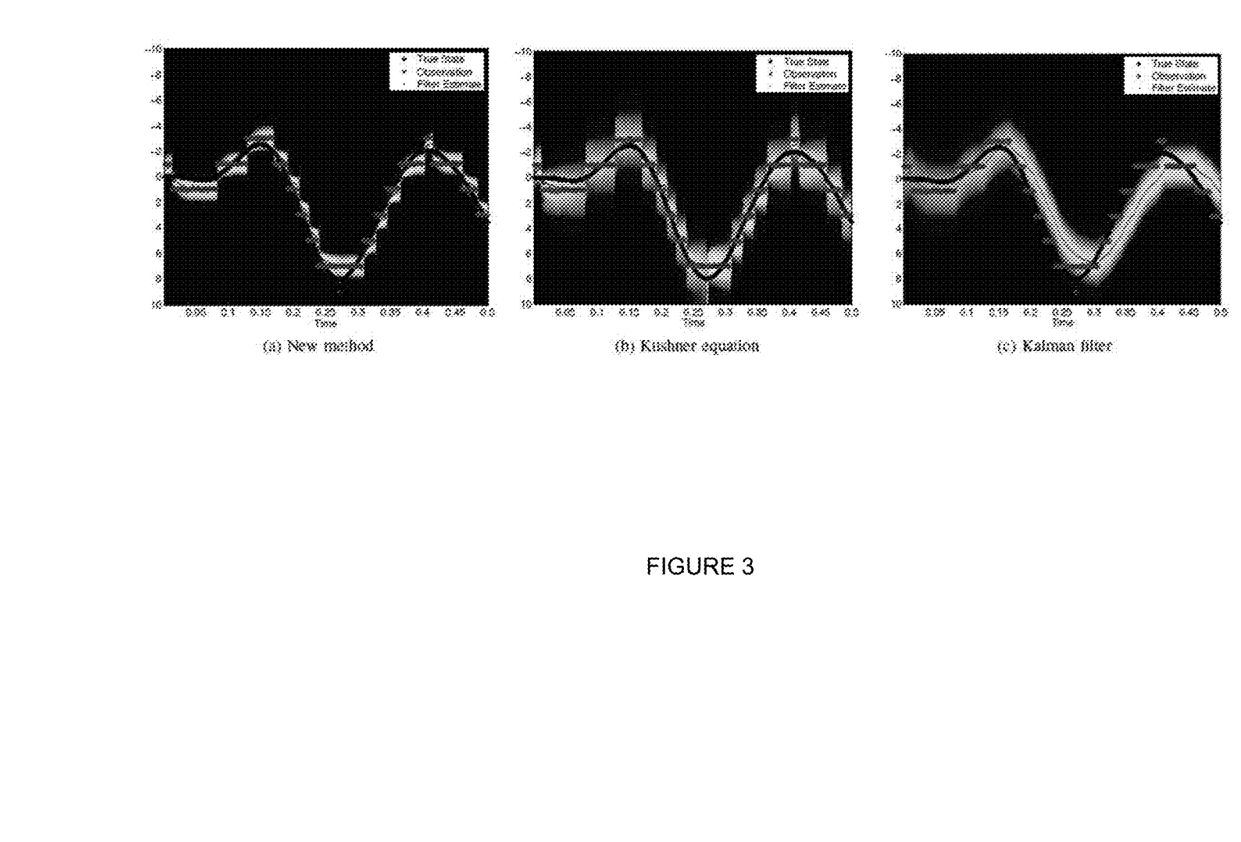
FIG. 3 shows a sample comparison of the nonlinear filtering algorithm with other filtering algorithms.

FIG. 3 shows a comparison between the Bayes-optimal nonlinear filter, Kushner filter, and Kalman filter. In this example, the true state dynamics are one-dimensional smoothed white noise, and observations are continuously available quantized measurements of state. The measurement model for Kushner's equation is dz=h(x)dt+gdB, and for the Kalman filter and the Bayes-optimal nonlinear filter: z=h(x)+gn where h(x) is a 10-level quantizer and g=½. B is standard Brownian noise, and n is standard white noise. Vertical axis is state x, horizontal axis is time t, and color indicates p(x,t). Black line is the true state x, pink line is the quantized observation and the red line is the maximum likelihood estimate returned by each filter. Both the new method and the Kushner equation correctly estimate the state, but the Kushner method overestimates the state uncertainty.

For the Kalman-Bucy filter, quantization error must be approximated as Gaussian noise with a standard deviation equal to half of the bin width. For the Kushner equation, the observed variable z is required to be the integral of the quantized state and therefore its variance grows without bound, so only its differential dz is used. Note that quantization causes uncertainty even with a deterministic (noise-free) observation process. This cannot be described accurately by linear filters such as Kalman-Bucy, and the extended Kalman filter fails because the observation model is not differentiable and thus cannot be approximated as a locally linear process.

At the moment of a transition between two different quantization levels, precise Information as to the underlying state is known (it must lie exactly on the transition threshold). Uncertainty in the state estimate grows between the time of transitions, but the set of possible values is bounded by the nearest transition thresholds. Therefore, between jumps of the observed variable, the state should gradually approach a uniform distribution bounded by the two nearest transition thresholds. Both the Bayes-optimal nonlinear filter and the Kushner filter show the expected behavior at the time of transitions, but the Kushner filter incorrectly predicts that there is nonzero probability of crossing a bit-transition boundary in the absence of a change in the quantized observation.

Generating 100 different time-series of filtered white noise, performance of the three filters can be compared. The mean-squared error in state estimates for the new method and the Kushner equation are not statistically different (Bayes*optimal: 0.345 (SD 0.06), Kushner: 0.341 (SD 0.06), p>0.5, t-test) and both are significantly better than Kalman-Bucy (0.922 (SD 0.40), p<0.0001). The average width (standard deviation) of the estimated conditional density p(x,t) was significantly less for the new method than for the Bayes-optimal filter and for the Kushner filter (0.548 vs. 1.768 for Kushner, p<0.0001), so the Kushner filter overestimated the uncertainty (probably due to sensitivity to time discretization in the simulation; in the theoretical continuous-time case the Kushner filter is expected to produce the correct variance).

The Bayes-optimal nonlinear filter is especially useful for high-rate (possibly low fidelity) measurements, or where the sample rate for measurements is similar to the rate at which estimates should be produced. For example, filtering noise out of an audio signal uses samples that occur at every timestep, and outputs are produced at every timestep. Filtering used to control automotive speed, aircraft navigation, or robotic controls have similar properties.

The Bayes-optimal nonlinear filtering method is not limited to estimating the state of only one variable. It is flexible enough to accommodate two conditionally-independent sensors $z_1(t)$ and $z_2(t)$. By conditionally-independent, $P(z_1,z_2|x)=(z_1|x)(z_2|x)$. The Bayes-optimal combined probability density may then be updated using:

$$\frac{\partial p(x, t)}{\partial t} = Fp(x, t) + [\log p(z_1 | x) - \log p(z_1, t)]$$
$$p(x, t) + [\log p(z_2 | x) - \log p(z_2, t)] p(x, t)$$

If the sensors are not conditionally independent, then the last line should be replaced by $[\log p(z_2|z_1, x) - \log p(z_2)|z_1, t)] p(x, t)$. This process can be generalized to an arbitrary number of sensors. Furthermore, if two independent estimates of the state density may be created so that $p_1(x,T)$ is based on data from $z_1(t)$ up to time T, and $p_2(x, T)$ is based on data from $z_2(t)$ up to time T, then the un-normalized density at time T from the combined sensor estimates as the product is obtained by the equation:

$$p(x,T)=p_1(x,T)p_2(x,T)$$

Combination of estimates from multiple sensors provides a considerable advantage over standard linear or parametric estimators, for which a combination of the mean estimates from different sensors (weighted by the inverse of the variances) is accurate only for unimodal Gaussian distributions. In particular, note that sensors can be combined even if they have different accuracy, different sampling intervals, time-varying noise, or ambiguity leading to multi-lobed density estimates.

Besides accounting for multiple sensors, the Bayes-optimal filter may also manage delayed measurements, such that sensor data is only available for z(t−□). There are two ways to manage such delayed measurements within this framework. The most straightforward is to estimate the delayed density p(x,t−□) and then to propagate forward for time □ open-loop using the Fokker-Planck equation ṗ=Fp with initial condition p(x,t−□). This provides an estimate of the current density, but requires forward propagation of the Fokker-Planck equation at every time, and it is difficult to use if there are multiple sensors with different time delays.

The second method is mathematically equivalent, but it depends upon calculation of the observation model p(z(t−□)|x(t)). This represents the information about the current value of state that is provided by the delayed observation (or, equivalently, the probability of the delayed observation given the current state). It will necessarily be less certain because time has passed since the observation. For example, if z(t)=x(t), then the observation model is p(x(t−□)|x(t)) which will spread the density (according to the backwards time Fokker-Planck equation). This delayed observation model can be directly used in the Bayes-optimal nonlinear filtering framework, and it allows straightforward combination of information from sensors with different delays.

This closed-loop system may be stable under circumstances that would lead to instability in standard closed-loop control. This is because the delayed measurement itself is not used for feedback, but instead it contributes to an estimate of the density of future state that may include values that are not out of phase with the true state.

The Bayes-optimal nonlinear filtering method provides other advantages. The framework allows for continuous data collection and filtering output rather than using discrete step-wise updates which causes delays. The nonlinear filtering method also is not required to follow the Nyquist criterion, which requires a sampling rate of twice the frequency of the signal, as the Bayes-optimal filter is not estimating frequencies, but probability densities. Thus, in some embodiments, additional filters are not necessary, removing any delay those filters may have caused.

Application of Bayes-Optimal Nonlinear Filtering Method to Biological Systems

The Bayes-optimal nonlinear filtering method provides stronger signal modelling for noisy environments in a variety of measurement models. One such environment in which such a filter is needed is in measuring signals in biological systems. Controlling biological systems is a very complex task, due to the presence of uncertainty and nonlinearity of the environment. Control strategies in the brain, executed by neural populations, have to take into account the sensory/motor noise, stimuli, or dynamics uncertainty, measurement quantization, nonlinear time-varying dynamics, and other potential causes of uncertainty.

The Bayes-optimal nonlinear filtering method can be used in an apparatus for diagnosis, treatment and maintenance of many clinical conditions that result in a disorder of the nervous system, a motor-neuron disorder, or a muscle disorder. In particular, individuals having, for example, but not limited to, cerebral palsy, brain damage, brain damage resulting from head trauma (for example, injuries received during wartime or in civil unrest), brain damage resulting from oxygen deprivation (for example, constriction of the umbilical cord prior to, during, and following birth), muscle loss (for example, AIDS, sarcopenia of old age, disuse atrophy, glucocorticoid-induced muscle loss, and prolonged spaceflight), paraplegic loss of all or part of a limb, muscle fatigue, loss of neural tissue, neurological disorders, stroke, or the like, may use the invention as disclosed herein. The invention may be used in the clinic, such as for use in physiotherapy and/or rehabilitation, or can be used by an individual in a normal home or work environment. For example, a surface electromyography device applying the Bayes-optimal nonlinear filter could provide feedback to a subject to encourage increased usage of muscles during rehabilitation, as described in more detail below.

Surface Electromyography Embodiment

An example biological system where measurements have a large amount of noise is the field of Electromyography (EMG), which measures the muscle electrical activity during muscle contractions as an electrical potential between a ground electrode and a sensor electrode. EMG can measure signals either directly within the muscle (invasive EMG) or on the skin above a muscle (surface EMG).

Invasive EMG is very accurate in sensing muscle activation, but is generally considered to be impractical for human-computer interaction (HCI) applications as it requires needle electrodes to be inserted through the skin and directly into muscle fibers. In contrast, surface EMG (sEMG), while less accurate, only requires that conductive sensors be placed on the surface of the skin. Surface EMG is fundamentally noisier than invasive EMG since motor unit action potentials (MUAPs) must pass through body tissue such as fat and skin before they can be captured by a sensor on the surface. Due to the high sensitivity of EMG sensors required to detect these signals, they also typically detect other electrical phenomena such as activity from other muscles, skin movement over muscles, and environmental noise, etc. The noisy sEMG signal has traditionally been considered of insufficient quality for accurate control. Thus, there is a need for a method of filtering the noisy signal to produce a high quality sEMG signal.

This can be done using a processor applying the Bayes-optimal nonlinear filtering method as described. Surface Electromyography firing rates are Poisson processes whose average rates are regulated by the corresponding continuous state variables. The Bayes-optimal nonlinear filtering method is flexible enough to accommodate Gaussian, Gamma, and Poisson measurement processes, as the framework utilizes the likelihood function $p(z|x)$.

A combination of sEMG sensors and a processor employing the Bayes-optimal nonlinear filtering algorithm to filter the noisy signal could provide a continuous real-time high quality signal that may be useful in research, biofeedback, control, and other areas. In some embodiments, a biofeedback device comprises at least one sEMG sensor detecting a sEMG signal, a processor receiving the sEMG signal and applying the Bayes-optimal nonlinear filter to produce a filtered signal, and a feedback device receiving the filtered signal and providing feedback based on the filtered signal.

Figure 4:
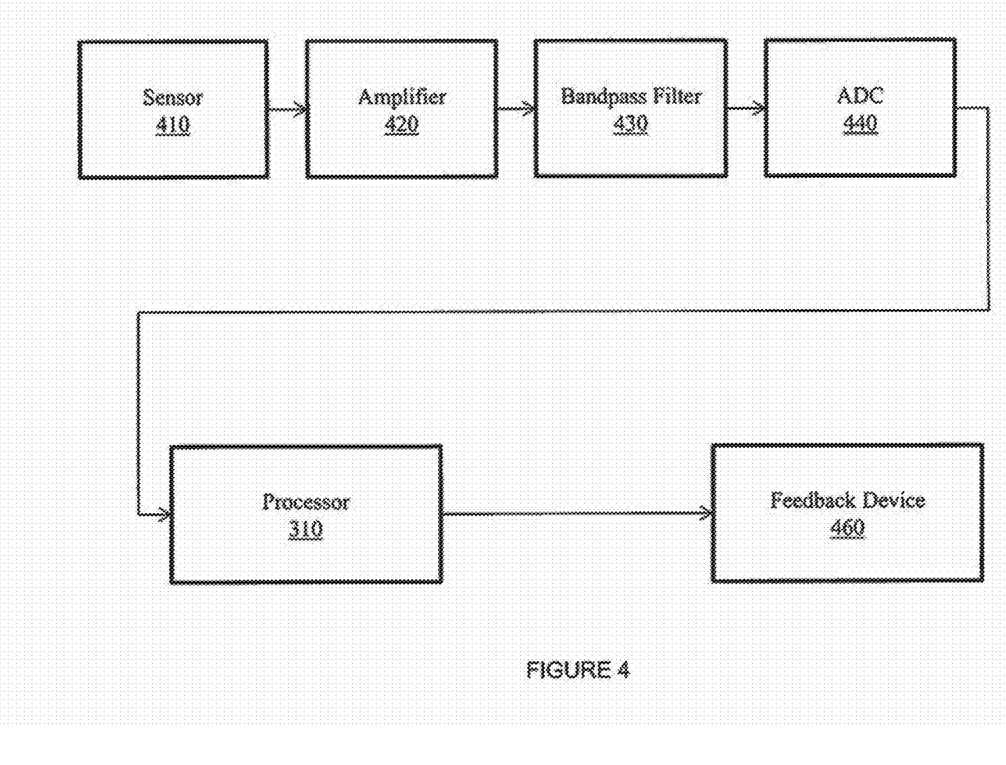
FIG. 4 shows a high level diagram of hardware components of a biomedical device that may be used to implement various aspects of the present disclosure in certain embodiments.

A high level flow diagram of a sEMG biofeedback device is illustrated in FIG. 4. This diagram is not intended to provide an exhaustive or complete illustration of every possible embodiment of hardware implementing the described filtering methods, but is provided for purposes of illustration only. In various embodiments, the components described herein may be performed in an order different from the particular order described or shown. In other embodiments, other components may be provided, or components may be eliminated, from the described diagram.

In some embodiments, a sensor 410 comprising electrodes on the surface of a subject measures muscle electrical activity. The sensor may be coupled with an amplifier 420, such as a high-impedance instrumentation amplifier or other differential amplifier, may be used to boost the signal captured, a bandpass filter 430 to filter frequencies too high or low to provide useful data, and an analog-to-digital converter 440 to quantize the signal to be used by a processor 210, and/or other components. The signal is then passed to a processor 210 that applies the Bayes-optimal nonlinear filter in order to determine the maximum likelihood estimation of the signal. This is then passed to the feedback device 460 in order to indicate to the subject the level of muscular activity at the sensor 410.

The sensor is placed upon the surface of the skin of a subject and held in place using a number of different means, such as, but not limited to, straps, self-adhesive straps, hook-and-loop fasteners, buckles, heat-activated adhesives, UV-activated adhesives, adhesive strips, magnetic strips, and the like. In some embodiments, sensors are integrated into wearable clothing or accessories.

Most sEMG is recorded with bandpass filters 430 set between 20 Hz and 500 Hz. However, the Bayes-optimal nonlinear filtering method allows for better performance at higher frequencies. Lower frequencies are less likely to contain useful information as they are less likely to contain information about rapid change, and long observation intervals are required to estimate the power in low frequency data. Therefore bandpass filters from 100 Hz to 1500 Hz are useful in capturing useful sEMG data before being passed on to the nonlinear filter, although other frequencies may be used in this filtering method. In some embodiments, the bandpass filter comprises a high pass filter, a half-wave or full-wave rectifying circuit, and a low pass filter.

Processor 210 applies the Bayes-optimal nonlinear filter to the signal and returns the maximum likelihood estimate to be sent to the feedback means and/or device. Non-transitory computer readable storage media, such as a storage device 220 or memory 230, may hold filter instructions and the probability distribution function to apply the nonlinear filter and update the probability distribution function as the signal is input into the processor.

A feedback means and/or device informs the subject that the system detects activity. In a sEMG system, the feedback may indicate the amount and degree of muscle movement detected. The feedback may be shown through any number of means, for example, the feedback may be through audio, visual, and haptic means and/or devices. These may indicate the amount and degree of muscle movement detected. A system may employ one or more types of feedback, as a combination could provide more information to a subject.

An audio device can be used with the system to provide an aural or audio feedback to the subject. Audio devices are well known to those in the art and can include speakers, resonators, and the like. Audio devices may indicate the amount and degree of muscle movement through variations of volume, frequency, tune, and the like. Audio devices are particularly useful for patients or individuals having poor or impaired sight.

Visual devices can be used to provide visual feedback to the subject. Visual devices are well known to those in the art and can include LEDs, computer monitors, tablet computer touchscreens, smartphone displays, and the like. Visual devices are particularly useful for patients or individuals having poor or impaired hearing.

Haptic devices can be used to provide a tactile or force sensation to a subject. A prominent example of haptic feedback is a smartphone's vibrate feature caused by a motor to alert a user. Haptic feedback devices may indicate the amount and degree of muscle movement through variations of force, intensity, frequency, and the like. Vibrational feedback is especially useful for situation when audio or visual feedback may be distracting to others around the user. In a biofeedback or control setting, vibration of the same muscles that is used for measurement of sEMG is useful to associate the muscle activity with the feedback. In a setting with sensors covering multiple body parts, this form of feedback would also more readily identify the muscle activity.

The system may comprise multiple components in wired or wireless communication. A wireless communication system that is used to transfer data from the sensor means and/or device, the processor, the feedback means and/or device, and other components could reduce the number of components applied or connected to a subject to reduce the weight and/or size of a device attached to subject. In some embodiments, the sensor and feedback device are applied to the subject, and the remaining components are spatially separated from those components. This may be beneficial, as separating components from a subject removes size restrictions on components not attached to the subject. A wireless communication system may use any suitable communication protocol as described above.

In some embodiments, multiple types of feedback means and/or devices are used in the system. In some embodiments, the feedback device is a smartphone in wireless communication with the other components. For example, a software application on a smartphone would be configured to receive the sEMG data via Bluetooth, provide audio/visual/haptic feedback to a subject, record trends over time, compare data with friends via a social network, remind a subject to exercise, and generally do things to encourage subjects to increase use (and hence strength/fitness) of the sensed muscle. Transmission could be configured to continuously stream data for real-time feedback of muscle activity or intermittent so that trends and average activities are accumulated over time with some sort of score provided intermittently or at the end of the day. In some embodiments, the software application controls the hardware components' power, monitoring rate, feedback functionality, and other such options. In some embodiments, the nonlinear filter is implemented on the sensor device, in the smartphone, or only as optional post-processing.

Figure 5:
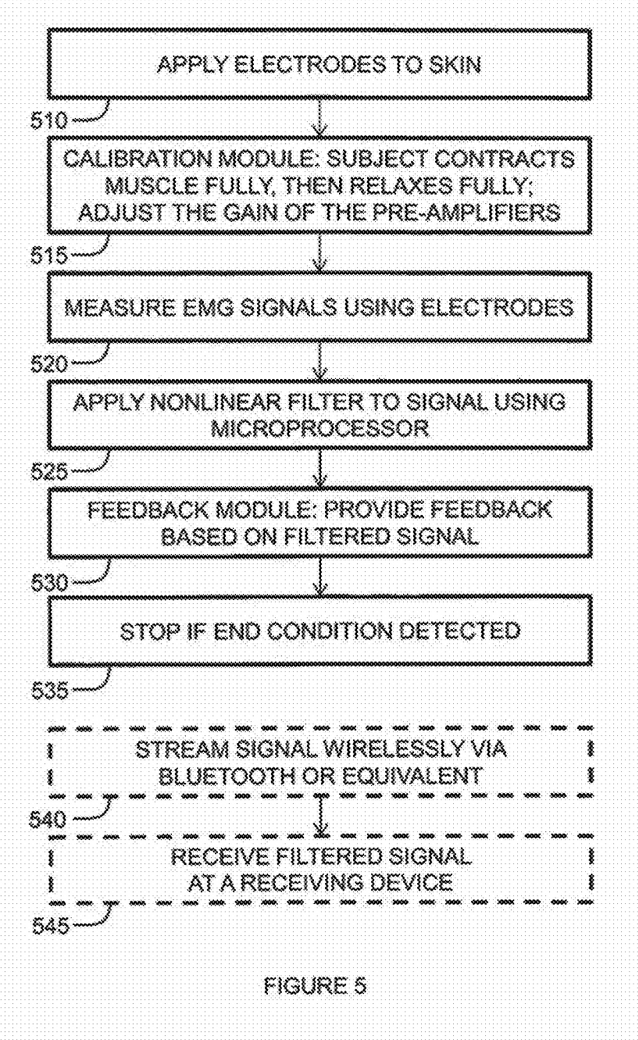
FIG. 5 shows a flow diagram of a method of use of an embodiment of a biomedical device utilizing a nonlinear filtering algorithm in accordance with an embodiment of the present disclosure.

A flow diagram of a method of use of an embodiment of a sEMG biofeedback device is depicted in FIG. 5. The electrodes of the sensor are applied to a subject's skin and held in place in step 510 to enable capture of human muscular activity. The sensor is then calibrated using a calibration module on the device in step 515 to capture the best possible signal. In some embodiments, to calibrate the device to the subject's signal, a subject will contract the muscles at the sensor location fully, and then relax those muscles fully. This allows the device to detect the full range of electrical activity of the muscles, and the gain of the pre-amplifiers on the sensor device is adjusted accordingly. In some embodiments, a device may automatically calibrate based on observed muscle activity without requiring the user to contract or relax fully. While this flow diagram illustrates calibration as occurring at an initial step, calibration may be ongoing to compensate for slow changes in skin impedance or contact with the skin, muscle fatigue, temperature, or other changes in signal strength.

Once calibrated, the sEMG device continually measures the subject's EMG signals in step 520 using the electrodes. The measured signal may be processed by additional components, such as an amplifier, bandpass filter, and/or analog-to-digital convert before being sent to the processor. The processor applies the nonlinear filter to the signal in step 525 to provide the maximum likelihood estimate of the data. As the processor filters the signal, it continually updates the probability distribution function. The filtered data is then sent to a feedback module in step 530 to provide continuous feedback based on the filtered signal, such as through vibrations, sound, light, or any other feedback that may indicate the electrical activity produced by the subjects muscles.

In some embodiments, a sEMG biofeedback device may comprise a termination module to detect when to stop capturing sEMG data in step 535. Example termination conditions can include, but are not limited to, a switch to turn off the device, removal of the sensor from a subject's skin, and a low battery warning.

In some embodiments, EMG data are streamed wirelessly, such as in step 540 and received at a receiving device in step 545. The EMG data streamed wirelessly may be at any point after the electrodes begin measuring EMG data. This can include streaming raw data to be filtered at a receiving device and/or streaming filtered data to be utilized by the receiving device.

FIGS. 6A-6D show components of an embodiment in accordance with the present disclosure. In this embodiment, the sEMG device comprises a sensor unit 600, shown in FIGS. 6A and 6B, and a control unit 620, shown in FIGS. 6C and 6D.

Figure 6A:
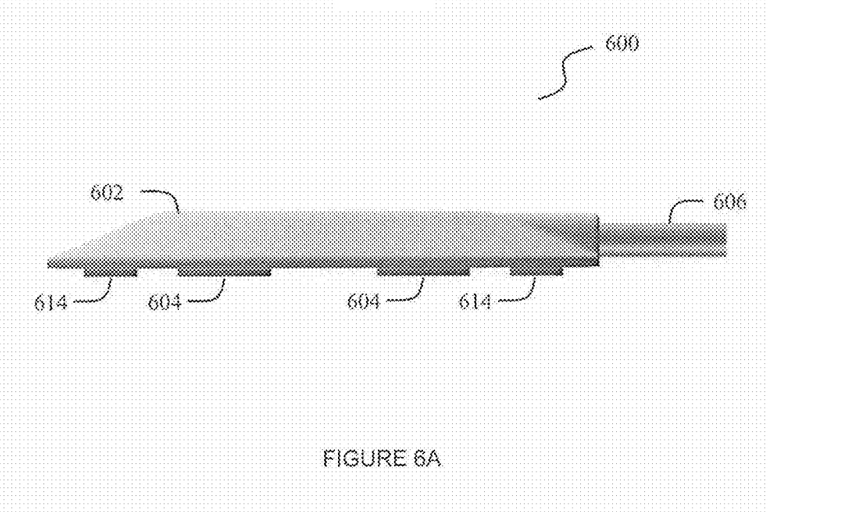
FIG. 6A shows a side view of a sensor in accordance with an embodiment of the present disclosure.
Figure 6B:
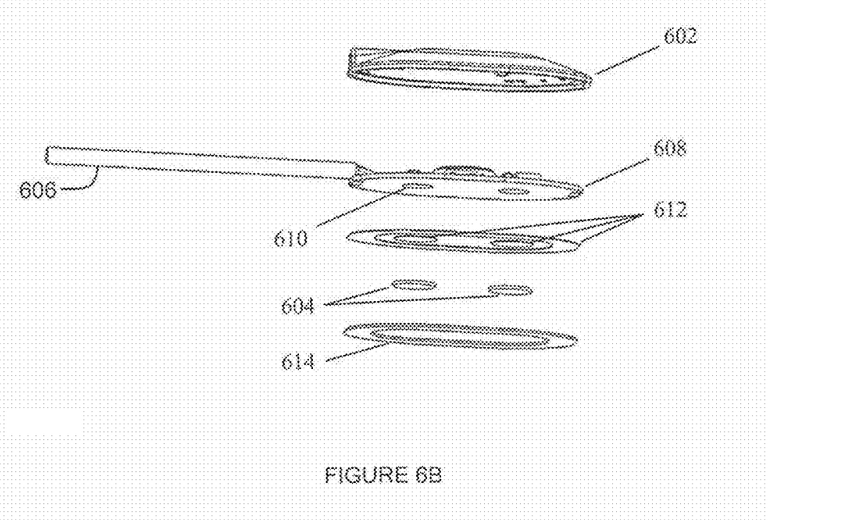
FIG. 6B shows an exploded perspective view of a sensor in accordance with an embodiment of the present disclosure.

In this example embodiment, the sensor unit 600 comprises a housing 602, a printed circuit board 608 (PCB), gold pads 610 on the PCB 608, conductive adhesive pads 612, electrodes 604, and ground electrode 614. The sensor unit 600 is applied directly to a subject's skin. The signal measure from the electrodes 604 is sent through wires 606 or wirelessly to the control unit 620. The wires 606 may also provide power to the sensor unit 600.

The configuration of the ground electrode contact 614 as a ring around the electrode contacts 604 is unique. In a typical sensor, the ground electrode is separate, and attaches to a subject using a conductive strap elsewhere. In the example embodiment, the ground electrode contact 614 is conveniently on the same surface as the electrode contacts 604, where the ground electrode ring provides some shielding from electromagnetic interference and ensures effective contact with the skin surface. In some embodiments, the electrodes are curved or bent near the edges to project into the skin to better sense electrical activity in the skin.

Figure 6C:
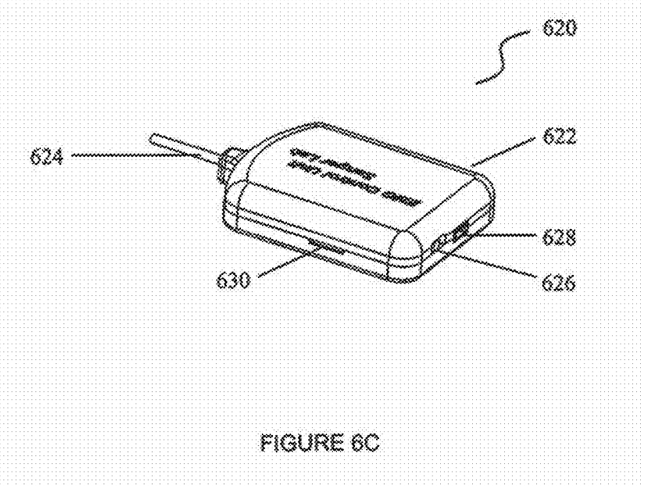
FIG. 6C shows a perspective view of a control unit in accordance with an embodiment of the present disclosure.
Figure 6D:
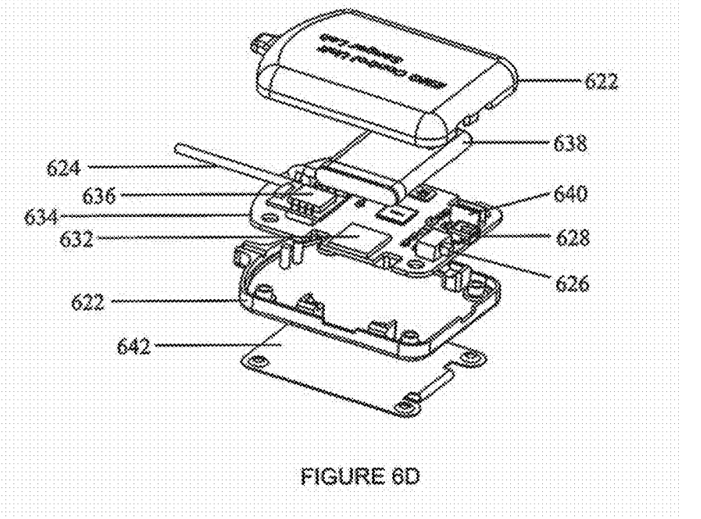
FIG. 6D shows an exploded perspective view of a control unit in accordance with an embodiment of the present disclosure.

In one embodiment, the control unit 620 comprises a housing 622, on/off switch 626, USB port 628, micro SD port 630, micro SD memory card 632, printed circuit board (PCB) 634, wireless chip 636, battery 638, JTAG (Joint Test Action Group) 640, microprocessor, and a clip 642. The on/off switch 626 is turned on for sensing and filtering EMG signals, and is turned off to conserve power. The USB port 628 is used to charge the battery and update the firmware. The micro SD memory card 632 may be removably inserted into the control unit 620. The micro SD card and separate nonvolatile memory chips are non-transitory computer readable storage media to store data, such as the raw and filtered EMG measurements, and instructions that when compiled by a processor apply the Bayes-optimal nonlinear filter to estimate the state of a signal. The wireless chip 636 may be used to send data to the sensor unit 600 to control sampling and power, to a feedback unit to provide feedback to a subject, to a computer to analyze the data, or any other device capable of wireless communication. The battery 638 powers the control unit 620 so it can be attached or worn on a user. The JTAG 640 is an interface for programming and debugging, and is the method for loading instructions into the processor memory. In some embodiments, the probability distribution is stored in the microprocessor's internal memory. In some embodiments, the maximum likelihood estimate is stored on the micros SD card.

In this example sEMG device, when the On/Off switch 626 is turned on, the electrodes 604 begin streaming measurements to the microprocessor. The microprocessor applies the nonlinear filtering instructions to continually filter the signal and update the probability distribution function, outputting and storing the maximum likelihood estimate on the micro SD card 632. This filtered data is then streamed wirelessly via the wireless chip 636 to a receiving device to provide feedback to the subject.

In some embodiments, amplifiers, filters, analog-to-digital converters, and other components are found on the sensor unit and/or the control unit. In some embodiments, a feedback means and/or device is attached to the sensor or the subject near the sensor in order to provide feedback at the sensor location.

The physical device noted above Is intended to be attached to a subject to measure and filter electrical signals produced by human muscular activity using surface Electromyography sensors. The processes described in capturing and filtering the signals are illustrated by the general system diagram in FIG. 4 and the general system methods in FIG. 5. However, FIGS. 4, 5 and 6A-6D are not intended to provide an exhaustive or complete illustration of every possible embodiment of hardware implementing the described filtering methods.

The components of the sEMG embodiments may vary depending upon the intended use. For uses where size is not a limitation, the system can be assembled using "off"-the-shelf components at a low cost. Such hardware can include, but is not limited to, sensors, amplifiers, transmitters, transceivers, receivers, microprocessors, non-transitory computer-readable storage media, motors, acoustic amplifiers, acoustic speakers, acoustic generators, haptic devices, batteries, photoelectric cells, piezoelectric devices, and other such components. The use of the Bayes-optimal nonlinear filtering method may allow for use of lower cost and lower quality components as the filter may compensate for that additional noise.

While the example embodiments illustrated in FIGS. 4-6 demonstrate a use in a biofeedback device, application of the Bayes-optimal nonlinear filter may be very useful for filtering noisy signals in other areas that would greatly benefit by this new filter. Examples include, but are not limited to, target tracking, real-time measurement for control systems in moving vehicles, digital processing of media, sensor fusion using multiple sensors on a single environment, human-computer interfacing, medical devices, and communication processing.

The foregoing descriptions of the embodiments of the invention have been presented for the purposes of illustration and description. It is not intended to be exhaustive or to limit the invention to the precise form disclosed. Many embodiments, modifications, and variations are possible in light of the above teaching. It is intended that the scope of the invention not be limited by this detailed description, but by the claims and the equivalents to the claims appended hereto.

Unless otherwise stated, all measurements, values, ratings, positions, magnitudes, sizes, and other specifications which are set forth in this specification are approximate, not exact. They are intended to have a reasonable range which is consistent with the functions to which they relate and with what is customary in the art to which they pertain.

All articles, patents, patent applications, and other publications which have been cited are hereby incorporated herein by reference.

INDUSTRIAL APPLICABILITY

This invention may be industrially applied to the development, manufacture, and use of surface electromyography devices, smartphone applications, and signal processors.

What is claimed is:
1. A feedback device comprising:
 a. a sensor component comprising at least one camera for measuring a signal indicative of hidden state comprises a plurality of state values, designated x; wherein the hidden state represents a location of the device within an environment; and wherein the signal comprises a plurality of time-varying signal measurements, designated z;
 b. a filtering component comprising: one or more processors; memory; and instructions stored in the memory that, when executed by the one or more processors, cause the one or more processors to:
i. determining an observation model, designated p(z|x), that relates a probability of signal measurements to the plurality of state values;
ii. determining a system dynamics model, designated F, that relates the hidden state to a change in state values based on dynamics of the environment;
iii. determining an initial estimate of a probability density function that characterizes a probability of one of said state values at an initial time;
iv. repeatedly updating a current estimate of the probability density function, designated p(x,t), that characterizes a probability of one of said state values based on a time, designated t; wherein the updated probability density function is based, at least in part, on:
   A. a product of the system dynamics model and the current probability density function; and
   B. a product of the current probability density function and a logarithm of the observation model;
v. outputting a maximum likelihood estimate based on the current estimate of probability density function, wherein the maximum likelihood estimate represents an estimate of a state value at each time; and
vi. generating an estimate of the plurality of state values, x, based on the maximum likelihood estimate at each time; and
c. a feedback component comprising a motor for producing feedback based on the estimate of the plurality of state values from the filtering component.

2. A method for generating feedback using a nonlinear filter to estimate a hidden state of an environment, wherein the hidden state comprises a plurality of state values, designated x, that characterize the environment over time; the method comprising:

receiving a noisy signal from a sensor component comprising at least one camera; wherein the noisy signal represents image data; wherein the noisy signal comprises a plurality of time-varying signal measurements, designated z;
determining an observation model, designated p(z|x), that relates a probability of signal measurements to the plurality of state values;
determining a system dynamics model, designated F, that relates the hidden state to a change in state values based on dynamics of the environment;
determining an initial estimate of a probability density function that characterizes a probability of one of said state values at an initial time;
repeatedly updating a current estimate of the probability density function, designated p(x,t), that characterizes a probability of one of said state values based on a time, designated t; wherein the updated probability density function is based, at least in part, on:
   a product of the system dynamics model and the current probability density function; and
   a product of the current probability density function and a logarithm of the observation model;
outputting a maximum likelihood estimate based on the current estimate of probability density function, wherein the maximum likelihood estimate represents an estimate of a state value at each time;
generating an estimate of the plurality of state values, x, based on the maximum likelihood estimate at each time; and
applying feedback with a feedback device based on the estimate of the plurality of state values, x, at each time;
wherein continuous-time nonlinear filtering of the noisy signal is acquired based on the observation model, p(z|x), and signal measurements, z.

* * * * *